United States Patent [19]

Bhattacharya et al.

[11] Patent Number: 5,380,867
[45] Date of Patent: Jan. 10, 1995

[54] SELECTIVE PRECIPITATION OF α-ARYL CARBOXYLIC ACID SALTS

[75] Inventors: Apurba Bhattacharya; John R. Fritch; Carl D. Murphy; Larry D. Zeagler; Carina A. McAdams, all of Corpus Christi, Tex.

[73] Assignee: Hoechst Celanese Corporation, Somerville, N.J.

[21] Appl. No.: 139,245

[22] Filed: Oct. 19, 1993

Related U.S. Application Data

[63] Continuation-in-part of Ser. No. 985,083, Dec. 2, 1992, Pat. No. 5,332,834.

[51] Int. Cl.⁶ .................... C07B 55/00; C07B 57/00
[52] U.S. Cl. .................. 548/344.1; 562/401; 562/490; 562/492
[58] Field of Search ............... 562/401, 490, 492; 548/344

[56] References Cited

U.S. PATENT DOCUMENTS

| | | | |
|---|---|---|---|
| 3,431,295 | 3/1969 | Suverkropp | 562/401 |
| 4,752,417 | 6/1988 | Inoue et al. | 562/401 |
| 4,946,997 | 8/1990 | Larsen et al. | 562/401 |
| 4,973,745 | 11/1990 | Blaschke et al. | 562/401 |
| 4,994,604 | 2/1991 | Jung et al. | 562/401 |
| 5,015,764 | 5/1991 | Manimaran et al. | 562/401 |
| 5,221,765 | 6/1993 | Patil et al. | 562/401 |

FOREIGN PATENT DOCUMENTS 0899023  6/1962  United Kingdom .

*Primary Examiner*—José G. Dees
*Assistant Examiner*—Dwayne C. Jones
*Attorney, Agent, or Firm*—James J. Mullen; Donald R. Cassady; Palaiyur S. Kalyanaraman

[57] ABSTRACT

A process is provided whereby S(+)-ibuprofen or R(−)-ibuprofen L-lysinate salt is produced by selective precipitation from a mixture containing enantiomers of ibuprofen and L-lysine. The quantity of L-lysine is not more than about a molar equivalent of the quantity of one of the enantiomers in the ibuprofen enantiomeric mixture. Upon precipitation of one ibuprofen enantiomer from the mixture, the overall precipitate and reaction mixture can be held for a sufficient period of time at a second temperature to allow the first precipitate to redissolve into the reaction mixture and the other ibuprofen enantiomer to precipitate out of the mixture in the salt form. Optically active ibuprofen is racemized by being heated at 100° C. to 300° C. in the substantial absence of other materials.

29 Claims, 5 Drawing Sheets

LYSINE REMOVAL BY
SECOND CROP CRYSTALLIZATION

LYSINE REMOVAL BY
AQUEOUS EXTRACTION

LYSINE REMOVAL BY EXTRACTION WITH AQUEOUS ACID

FREE S(+)-IBUPROFEN FROM LYSINATE SALT

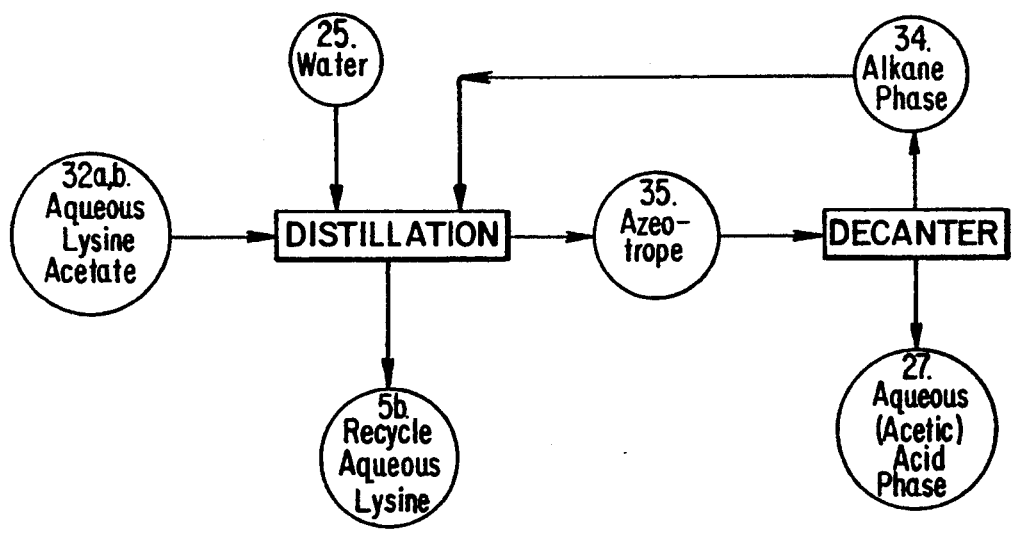
Fig.6 REMOVAL OF HOAc FROM LYSINE ACETATE
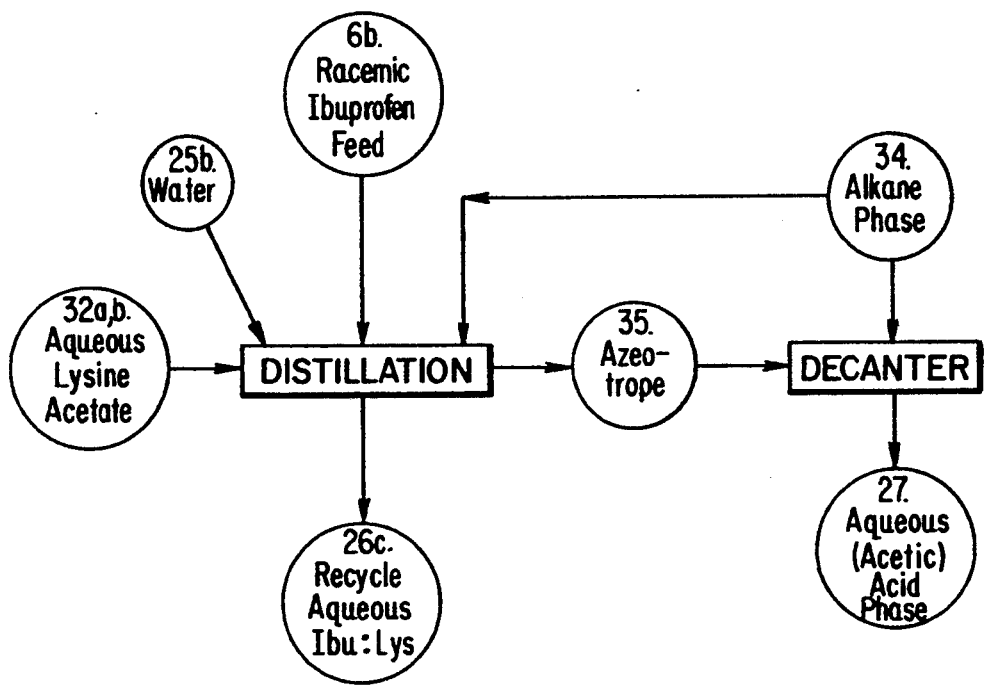
Fig.7 REMOVAL OF HOAc FROM LYSINE ACETATE WITH IBUPROFEN

RECOVERY OF FREE AQUEOUS LYSINE WITH CARBON DIOXIDE

SELECTIVE PRECIPITATION OF α-ARYL CARBOXYLIC ACID SALTS

RELATED APPLICATIONS

This patent application is a continuation-in-part application of pending U.S. Pat. No. 5,332,834 having an issue date of Jul. 26, 1994, (patent application Ser. No. 07/985,083 filed Dec. 2, 1992).

FIELD OF THE INVENTION

The present invention relates to selective crystallization of the desired salt of an α-aryl carboxylic acid from a mixture containing an α-aryl carboxylic acid and a suitable amino acid. By appropriate choice of the amounts of reactants, time, and temperature, the process enables selective crystallization of the desired diastereomer salt. Repetition of various facets of this process affords high yields of the desired salt in good enantiomeric excess, which may then be optionally acidified to afford optically active α-aryl carboxylic acid.

BACKGROUND OF THE INVENTION

α-Aryl carboxylic acids are well known non-steroidal anti-inflammatory (NSAI) drugs. An example is ibuprofen (Formula 1) which is typically a racemic mixture of the S(+)- and R(−)-enantiomers.

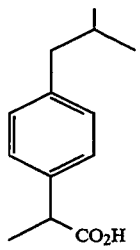

Studies have indicated that the S(+)-isomer is more pharmacologically active than the R(−)-isomer, see, for Example. A. Avgerinos et al, *Chirality*, Vol. 2, 249 (1990). Attempts have been made recently to isolate the S(+)-isomer from the racemic mixture.

U.S. Pat. No. 5,015,764 (Assignee: Ethyl Corp.) discloses a process whereby the triethylamine salt of racereit ibuprofen is treated with chiral α-methylbenzylamine (MBA). The MBA salt of one isomer of ibuprofen separates as crystals and is filtered off. The triethylamine salt of the other isomer is isolated from the tiltrates, is separately racemized, and is then treated again as described above.

U.S. Pat. No. 4,994,604 (Assignee: Merck&Co.) teaches S-lysine for the resolution of racemic ibuprofen. Racemic ibuprofen and S-lysine are combined in equimolar quantifies in a solvent system, such as ethanol:water so that the solution is supersaturated in both R, S and S, S salts. The solution is first aged at around 30° C., and then seeded at around 25° C. with a fairly large amount of S-ibuprofen-S-lysinate. This allows the S-ibuprofen-S-lysinate from the racemate mixture to crystallize out. The mother liquor, after filtration, is seeded again to precipitate additional S-salt. Repetition of this process gives the S-ibuprofen-S-lysinate as crystals, and leaves the R-salt in the solution, thus allowing a recovery of 50% of the original amount of the racemic ibuprofen as S-ibuprofen lysinate salt.

U.S. Pat. No. 5,189,208 (Assignee: Ethyl Corporation) discloses a process for obtaining a substantially pure enantiomer of ibuprofen. The process utilizes first an enantiomerically enriched mixture of ibuprofen obtained from kinetic resolution, diastereomeric crystallization, or asymmetric synthesis processes. This enriched mixture is dissolved in a solvent and solid racemic ibuprofen is separated, leaving a mother liquor comprising the solvent and the enriched enantiomer substantially free of the other enantiomer.

Other prior art references which are pertinent include U.S. Pat. Nos. 3,431,295; 4,752,417; 4,994,604; British Patent Specification No. 899,023; and pending U.S. patent application Ser. No. 07/649,782, filed Jan. 31, 1991 (A. Bhattacharya et al.).

All of these prior art references are submitted pursuant to 37 CFR 1.56, 1.97, and 1.98. These references, patent applications, and patents are incorporated herein by reference in their entirety.

Other methods such as enzymatic resolution and chromatography have also been suggested for resolution. The disadvantage with such processes is that they are time-consuming, and the yields are low.

While resolution of racemic mixtures is known, generally such processes lead to yields of a maximum 50% of one isomer, and 50% of the other isomer. In order to get higher yields of one isomer, the other isomer, after isolation, must be separately racemized to eventually isolate more of the desired isomer. Such processes generally employ conditions that are so different from the resolution step that the two are incompatible for efficient recycle. Because optically active α-aryl carboxylic acids and their salts have greater commercial value than racemic acids and their salts, there is a growing interest in finding improved methods to selectively crystallize such salts from solutions containing the racemic acid and a chiral amine.

SUMMARY OF INVENTION

The inventive process includes selectively crystallizing a salt of optically active α-aryl carboxylic acid in more than 50%, yields with recycle and in high enantiomeric excess from a solution typically containing the racemic form of the same acid and a suitable optically active amino acid. Suitable amino acids include optically active lysine, arginine, histidine. The α-aryl carboxylic acid is of the formula $Ar(R)CHCO_2H$, wherein R is selected from the group consisting of $C_1$–$C_8$ alkyl and $C_1$–$C_8$ substituted alkyl, and Ar is selected from the group consisting of phenyl, substituted phenyl, 2-naphthyl, substituted 2-naphthyl, 2-fluorenyl, and substituted 2-fluorenyl. The inventive process includes (a) forming a solution of a mixture of enantiomers of α-aryl carboxylic acid in a suitable solvent; (b) adding a suitable optically active amino acid such that the amount of said amino acid is not more than about a molar equivalent of the desired enantiomer in said racemic acid; (c) optionally seeding the above mixture with pure crystals of the salt of said α-aryl carboxylic acid and said amino acid and letting it form crystals of the desired salt, typically at a certain temperature range, e.g. about −10° C. to about +10° C. for a first enantiomer and about +15° C. to about +25° C. for the second enantiomer, over a period of about 0.25 to about eight (8) hours for the first enantiomer and about eight (8) hours to about 96 hours for the second enantiomer; (d) separating the crystals of the desired salt enriched in one enantiomer of said acid; (e) substantially evaporating the solvent to isolate the other enantiomer of the α-aryl carboxylic acid; (f) racemizing said other enantiomer of step (e) to give racemic α-aryl carboxylic acid which is then recycled to step (a) of the next batch, thus ultimately converting all racemic α-aryl carboxylic acid into almost exclusively the salt of one enantiomer; and (g) optionally acidifying the salt of step (f) to liberate free optically active α-aryl carboxylic acid.

In another facet of the present invention, there is provided a process which includes (a) forming a solution of a mixture of first and second enantiomers of α-aryl carboxylic acid in a suitable solvent; (b) adding a suitable optically active amino acid such that the amount of said amino acid is not more than about a molar equivalent of one enantiomer; (c) precipitating from said mixture at a first temperature a first salt of said optically active amino acid and said α-aryl carboxylic acid enriched in said first enantiomer; (d) increasing the temperature of said mixture to a second temperature; (e) holding said (reaction) mixture containing said precipitated first salt for a sufficient period of time at said temperature whereby said precipitated first salt redissolves into said (reaction) mixture and a second salt of said optically active amino acid and said α-aryl carboxylic acid enriched in said second enantiomer precipitates; and (f) separating the precipitated crystals of said second salt from the reaction mixture.

The inventive process is described in detail below in connection with selective crystallization of the L-lysinate salt of S(+)-ibuprofen from typically racemic ibuprofen and L-lysine. [The term S-ibuprofen and S(+)-ibuprofen are hereinafter used interchangeably, as are the terms R-ibuprofen and R(−)-ibuprofen.] Although the instant invention is described herein as a process for resolving racemic ibuprofen, it is potentially useful to prepare optically active α-aryl carboxylic acids in general whether or not the initial acid feed is racemic. It is to be understood that throughout the specification, "lysine hydrochloride" refers to the monohydrochloride salt of lysine, and "protonated cation of lysine" refers to the toonotation of lysine. L-lysine, S-lysine, (+)-lysine, and d-lysine are different names for the same enantiomer; D-lysine, R-lysine, (−)-lysine, and l-lysine are different names for the other enantiomer.

BRIEF DESCRIPTION OF DRAWINGS

The invention is described in detail below with reference to FIGS. 1 through 8 which are flow diagrams of procedures of the present invention as described in the examples which follow.

DESCRIPTION OF THE PREFERRED EMBODIMENTS

Figure 1:
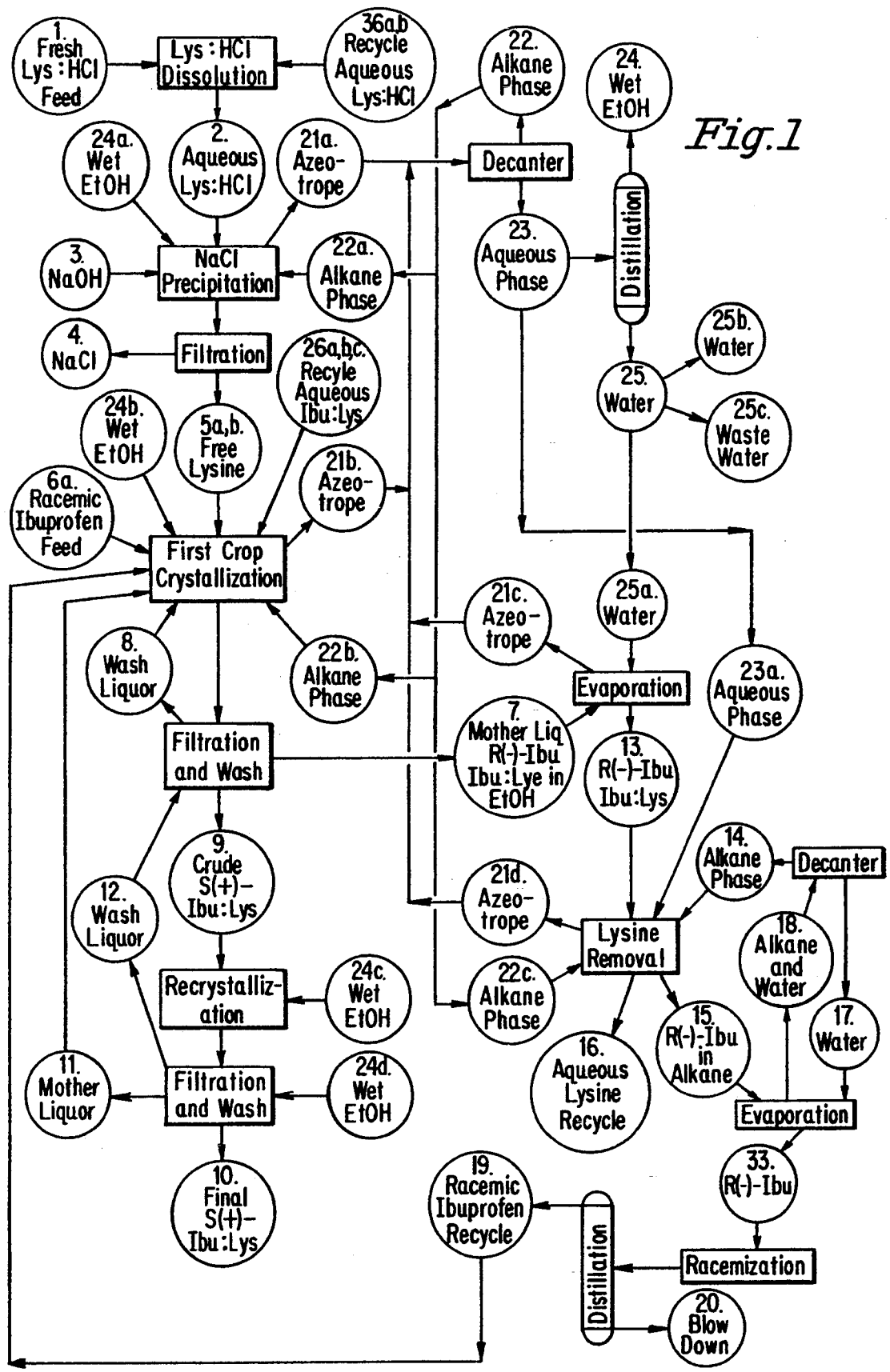

In one embodiment, the invention discloses a novel process to selectively crystallize salts of optically active ibuprofen from solutions containing racemic ibuprofen and an optically active amino acid which forms the salt with the desired enantiomer of ibuprofen. The process, unlike conventional resolution methods, yields, after recycle over several batches, the desired isomer in high yields with high enantiomeric excess, while using not more than about a molar equivalent of the amino acid based on the desired enantiomer of ibuprofen in any single batch. Furthermore, after removing the desired isomer salt from the mix, the undesired isomer of ibuprofen present in the mother liquors is racemized, preferably without any added catalyst or solvent. Such racemization is environmentally desirable, and permits direct recycle of the undesired enantiomer thus ultimately resulting in virtually complete conversion of racemic ibuprofen feed to the salt of the desired enantiomer. The following description illustrates the isolation of the salt of S-ibuprofen.

The process typically begins by forming the salt of racemic ibuprofen with an optically active amino acid such as, for example, L-lysine. The reaction is conducted in a solvent mixture of a suitable alcohol and water. Suitable alcohols are those that can dissolve the ibuprofen and are also miscible with water. Examples include, but are not limited to, methanol, ethanol, n-propanol, isopropanol, 1-butanol, 2-butanol, isobutyl alcohol, t-butyl alcohol, 1-pentanol, 2-pentanol, 3-pentanol, 2-methyl-1-butanol, 2-methyl-2-butanol, 3-methyl-2-butanol, 3-methyl-1-butanol, neopentyl alcohol, and the like, with ethanol and methanol being the preferred, and ethanol the most preferred. Generally the ibuprofen is dissolved in the alcohol to which the requisite amount of an aqueous solution of the amino acid, L-lysine, is added. The amount of water in the total mix ranges generally from 1 part of water for 99 parts of the alcohol to 10 parts of water for 90 parts of the alcohol, typically from 2 parts of water for 98 parts of the alcohol to 7 parts of water for 93 parts of alcohol, and preferably from 3 parts of water for 97 parts of the alcohol to 5 parts of water for 95 parts of the alcohol. The amount of the amino acid in the mixture is not more than about a molar equivalent of the S(+)-ibuprofen in the racemic acid, typically about 0.6 to 1.0 molar equivalent, and preferably about 0.7 to 0.9 molar equivalent. The same ratios are preferable with respect to other α-aryl carboxylic acid/amino acid pairs. The concentration of dissolved solids in the alcohol-water mixture ranges from about 3 to about 30 weight percent.

The above mixture is then partially distilled with a suitable azeotroping agent to lower the water content of the mixture to about 0.5 to 12.0 wt %. Suitable water-immiscible azeotroping agents and organic solvents for this and other steps of the present process include, but are not limited to benzene, toluene, ethylbenzene, xylene, chlorobenzene, or other aromatics; methyl t-butyl, ethyl t-butyl, ethyl n-butyl, di-n-propyl, diisopropyl, dibutyl, or other ethers; methyl, ethyl, isopropyl, butyl, propyl, isobutyl, t-butyl, or pentyl acetate, propionate, butyrate, isobutyrate, or valerate, or other esters; linear, cyclic, or branched pentanes, heptanes, hexanes, octanes, or nonanes; other $C_4$ to $C_{10}$ hydrocarbons, ethers, and esters; and the like, with cyclohexane, heptane and cycloheptane being the preferred, with cyclohexane and heptane being the most preferred. The mixture is then cooled to about −10° C. to about 10° C., preferably at about −10° C. to about 5° C., and typically at about −5° C. to about 5° C., to start crystallization of S(+)-ibuprofen lysinate salt. The mixture may optionally be seeded with pure crystals of S(+)-ibuprofen lysinate to induce crystallization. Whether seeded or not, the solution is maintained at the above-described temperature for a period of about 0.25 to 8 hours. If seeding is desired, usually a small amount of seed, a few crystals, is sufficient. The separated first crop crystals of crude S-ibuprofen L-lysinate may be separated by processes such as filtration, centrifugation and the like. This first crop is highly enriched, generally to more than 90%, in the S-form of ibuprofen.

The first crop crystals of crude S(+)-ibuprofen L-lysinate may be recrystallized as follows. The crystals are mixed with an alcohol-water mixture of the types described above, at about 40° to 80° C. generally, and about 50° to 78° C. preferably, to form about a 3 to 40 wt % mixture. This mixture is then cooled to about −10° C. to about 10° C. for about 0.25 to 8 hours to crystallize pure S(+)-ibuprofen L-lysinate. The mixture may be optionally seeded with the crystals of S(+)-ibuprofen L-lysinate to induce crystallization, if seeding is desired. Enantiomeric purities of more than 99% in the S(+) form of ibuprofen may be obtained.

Alternatively, the recrystallization may be carried out in a solvent with higher water content, e.g. 7% water and 93% ethanol to 20% water and 80% ethanol and preferably 10% water and 90% ethanol, to form the monohydrate of the S(+)-ibuprofen L-lysinate. The mixture may be optionally seeded with crystals of S(+)-ibuprofen L-lysinate monohydrate to induce crystallization, if seeding is desired. Enantiomeric purities of more than 99% in the S(+) form of ibuprofen may be obtained.

The crude S(+)-ibuprofen lysinate from first crop crystallization is optimally washed with 0° C. absolute ethanol. Recrystallized S(+)-ibuprofen lysinate (as the monohydrate) can be washed with 0° C. 98:2 ethanol:-water without losing the water of hydration, and the resulting wash liquor can be used to wash the crude S(+)-ibuprofen lysinate from first crop crystallization.

The filtrates or mother liquor [stream 7] from the first crop crystallization (Example 2) contain R-enriched ibuprofen free acid, and small amounts of lysine as the lysinate salt of ibuprofen. Most of this lysine may optionally be removed and recovered from this R(−)-enriched ibuprofen free acid by any of a number of procedures, either individually or in combination, such as Examples 4, 5, 8, 9, 10, and 24 below, (FIGS. 2–4 and 8) or as follows. The filtrates may be concentrated azeotropically to reduce the water content of the filtrates to about 0.01 to 3 wt %. The concentrated tiltrates may then be cooled to about 0° C. to 35° C. to deposit a second crop of ibuprofen lysinate. Alternately, a nonsolvent such as, for example, hexane may be added to the mixture to precipitate the second crop ibuprofen lysinate. This second crop ibuprofen lysinate salt which has an S/R enantiomeric ratio of about 20:80 may then be recycled to the next batch's first crop crystallization of crude S(+)-ibuprofen L-lysinate.

The mother liquors after removing the second crop ibuprofen lysinate salt may be evaporated to leave behind a residue of substantially lysine-free R-enriched ibuprofen which is racemized as described below, and then recycled to first crop crystallization of crude S(+)-ibuprofen lysinate.

Racemization of the R-enriched ibuprofen may be accomplished by several methods. For example, U.S. Pat. No. 5,015,764 referred to above, describes racemization in the presence of triethylamine in octane for 18 hours, or in concentrated hydrochloric acid for 72 hours, or in refluxing isopropanol in the presence of NaOH for 16 hours. U.S. Pat. No. 4,946,997 describes racemization in refluxing isopropyl acetate in the presence of acetic anhydride and sodium acetate, or by heating ibuprofen acid chloride with sodium ibuprofenate. Ruchardt et al, *Angew. Chem. Int. Ed. Engl.,* Vol. 23, page 162 (1964) discloses racemization by refluxing in acetic anhydride and pyridine. While such methods can be used for racemization in the instant case, they, however, have several disadvantages. They generally consume reagents which produce by-products necessitating elaborate separation and waste disposal procedures. They also are carried out in solvents requiring procedures for separation and recovery. Some of the reagents and solvents are also toxic.

It has been found, as an aspect of the present invention, that compositions which consist essentially of an optically active α-aryl carboxylic acid, free from solvents, catalysts, and the like, can be spontaneously racemized by heating under an inert atmosphere. The inert atmosphere may be provided by nitrogen, argon, and the like. The temperature of heating is generally in the range 100° C. to 300° C., typically about 100° C. to 250° C., and preferably about 200° C. to 250° C. The duration of heating is usually about one (1) to ten (10) hours generally, two (2) to eight (8) hours typically, and three (3) to six (6) hours preferably. Such racemization can also be achieved by heating in air to a temperature generally in the range 50° C. to 300° C., typically about 80° C. to 280° C., and preferably about 100° C. to 250° C. The duration of heating is usually about one (1) to ten (10) hours generally, two (2) to eight (8) hours typically, and three (3) to six (6) hours preferably. As used herein, the term "consisting essentially of" refers to a pure isomer or a mixture of isomers of the same α-aryl carboxylic acid, i.e. the R and S isomers, but specifically excludes other ingredients such as solvents, catalysts, and the like, that would alter the basic and novel characteristics of the invention. The racemization conditions depend on the thermal properties of the material, such as, for example, thermal decomposition characteristics. Such properties may be ascertained by analytical techniques known to those skilled in the art, such as thermal gravimetric analysis, differential scanning calorimetry, and the like. The goal is to find conditions where thermal decomposition of the material during heating would be minimal. The progress and completion of the racemization may be ascertained by analytical techniques such as, for example, chiral High Pressure Liquid Chromatography (chiral HPLC). Heating R-ibuprofen or R-enriched ibuprofen under the above-described conditions effectively converts half of the optically active acid to its mirror image, thus producing the racemic modification as the product. Similar racemization may be performed on S-ibuprofen or S-enriched ibuprofen also.

Racereit ibuprofen obtained from the racemization reaction above may be subjected to selective crystallization as described above to isolate more S-ibuprofen lysinate. Preferably, the racemic ibuprofen from the racemization reaction is vacuum distilled at about 150° C. to 250° C. The distillation residue, with recycles fully implemented, weighs generally about 2% of the final S-ibuprofen lysinate product weight. The distilled, racemized ibuprofen is recycled to the next batch's selective crystallization to isolate more S-ibuprofen lysinate. By combining the racemization and selective crystallization, the inventive process produces S-ibuprofen L-lysinate in yields substantially more than 50%, generally close to 100%, based on the amount of racemic ibuprofen and lysine feeds.

The previously described removal and recovery of residual lysine from the R(−)-enriched ibuprofen free acid in the first crop crystallization mother liquor [stream 7] is desirable, because most such lysine undergoes conversion to amides of lysine with or without ibuprofen during racemization and distillation (Example 6). However, procedures for such removal and recovery of lysine are not essential and may be deleted, because racemic ibuprofen is distilled off from lysine and its amide decomposition products (Example 6), and the losses of lysine and ibuprofen to the residue of such distillation would not be prohibitive.

Although the process has been described above for the L-lysinate salt of S(+)-ibuprofen, substantially the same process can be used for selective crystallization of salts of other similar optically active α-aryl carboxylic acids using other similar optically active amino acids. The α-aryl carboxylic acids include, but are not limited to, naproxen, fenoprofen, indoprofen, ketoprofen, flurbiprofen, pirprofen, suprofen, cicloprofen, minoxiprofen, carprofen, benoxaprofen, bisiprofenum, fluprofen, clidimac, tertiprofen, hexaprofen, mexoprofen, pranoprofen, and the like. The amino acids include arginine and histidine.

The S(+)-ibuprofen L-lysinate may optionally be acidified to yield the free S(+)-ibuprofen. Suitable acids include acetic acid, carbonic acid, formic acid, propionic acid, $C_4$ to $C_5$ acids, hydrochloric acid, sulfuric acid, and the like. Suitable solvents include hexane, heptane, cyclohexane, xylene, and the other aforementioned solvents. The solvent is preferably, but not necessarily, the same as the azeotroping agent. In a typical process, the salt is treated, in a two-phase mixture of an organic solvent and water, with hydrochloric acid. L-Lysine hydrochloride forms and stays in the aqueous layer, while free acid S(+)-ibuprofen stays in the organic layer. The two layers are separated and S(+)-ibuprofen may be isolated by removing the organic solvent. L-Lysine hydrochloride in the aqueous layer may be converted to L-lysine which may then be recycled in the selective crystallization process. If acetic acid is used in the process, L-lysine acetate forms in the process, which may be isolated from the aqueous layer and processed to free L-lysine by lysine acetate cracking described below in the Examples.

The following examples are provided for purposes of illustration only and not by way of limitation. The various steps described in Examples 1-14 are illustrated schematically in FIGS. 1 to 7.

EXAMPLE 1

Precipitation of NaCl from Aqueous Lysine

Referring to FIG. 1, a mixture containing L-lysine hydrochloride (53.48 g, 0.2928 mole) and water (53.48 g) [stream 2, FIG. 1] is added to a stirred mixture containing sodium hydroxide (11.71 g, 0.2928 mole) [from stream 3] and ethanol (221.3 g) [from stream 24a] at 60° C. Heptane [stream 22a] and ethanol [stream 24a] are added to the resulting stirred mixture as an azeotrope [stream 21a] of water, ethanol, and heptane is removed by distillation at atmospheric pressure until the weight ratio of water:ethanol:lysine is lowered to 7:93:17.988. The resulting mixture is filtered hot to remove a solid [stream 4, 17.11 g] consisting mostly of NaCl from a solution [stream 5a] containing free lysine.

EXAMPLE 2

First Crop Crystallization of S(+)-Ibuprofen Lysinate from Racemic Ibuprofen in Aqueous Ethanol To a stirred mixture containing S(+)-ibuprofen (0.538 moles, 110.98 g), R(−)-ibuprofen 0.597 moles, 123.11 g), L-lysine (0.43023 moles, 62.895 g), ethanol (606 g), and water (ca. 125 g) [from streams 5a,b; 6a; 8; 11; 19; 24b; and 26a,b,c; FIG. 1] is added heptane [from stream 22b] and ethanol [from stream 24b] as an azeotrope [stream 21b] of water, ethanol, and heptane is removed by distillation at atmospheric pressure until the weight ratio of water: ethanol: lysine is lowered to 6:94:9.747. The stirred, undistilled residue is cooled to 25° C. and seeded with S(+)-ibuprofen lysinate crystals (143 mg). The stirred mixture is seeded with two additional 143 mg portions of S(+)-ibuprofen lysinate crystals, one after the stirred mixture has been cooled further to 0° C. and the other fifteen minutes later. After the mixture is stirred at 0° C. for 4 hours, the resulting precipitate is filtered from the mother liquor [stream 7] and then washed with a mixture [stream 12] containing ethanol (138 g) and water (12 g). The washed precipitate [stream 9] is the first crop crude S(+)-ibuprofen lysinate (0.3442 mole, 121.32 g dry basis) with an ibuprofen S/R ratio of 94:6. The wash liquor [stream 8] is recycled to the next batch's first crop crystallization of S(+)-ibuprofen lysinate.

EXAMPLE 3

Recrystallization of S(+)-Ibuprofen Lysinate

First crop crude S(+)-ibuprofen lysinate [stream 9, FIG. 1, 0.3442 mole, 121.32 g dry basis] is dissolved in a stirred mixture [stream 24c, FIG. 1 ] containing ethanol (357 g) and water (31 g) at 70° C. The resulting stirred mixture is cooled to 25° C., seeded with S(+)-ibuprofen lysinate monohydrate crystals (200 mg), and then cooled further to 0° C. for 4 hours. The resulting precipitate is filtered from the mother liquor [stream 11 ] and then washed with a mixture [stream 24d] containing ethanol (138 g) and water (12 g). The washed precipitate [stream 10] is pure S(+)-ibuprofen lysinate monohydrate (0.2837 mole, 100 g dry basis) with an ibuprofen S/R ratio of >99.5:1. The wash liquor [stream 12] is used to wash the next batch's crude S(+)-ibuprofen lysinate from first crop crystallization.

EXAMPLE 4

Evaporation of Solvent from the Mother Liquor of First Crop Crystallization

Water and ethanol are removed as azeotrope stream 21c by distillation in an evaporator from a mixture [stream 7; FIG. 1] containing S(+)-ibuprofen (0.2145 moles, 44.25 g), R(−)-ibuprofen (0.5763 moles, 118.89 g), L-lysine (0.08603 moles, 12.577 g), ethanol (ca. 570 g), and water (ca. 36.4 g). During the distillation, water [30 g, stream 25a] is injected into the base of the evaporator to help strip out the last traces of ethanol and to prevent formation of amides and ethyl esters. The molten evaporation residue [stream 13] contains S(+)-ibuprofen (0.2145 moles, 44.25 g), R(−)-ibuprofen (0.5763 moles, 118.89 g), and L-lysine (0.08603 moles, 12.577 g).

EXAMPLE 5

Second Crop Crystallization of Ibuprofen Lysinate

Figure 2:
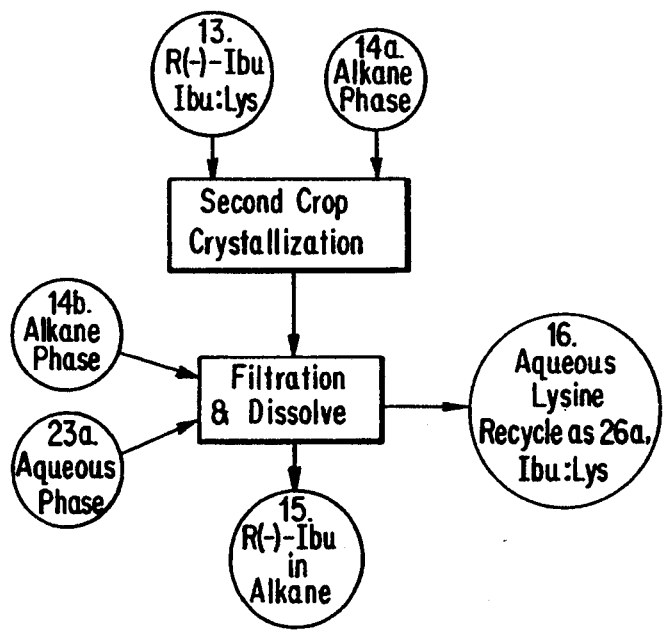
Figure 3:
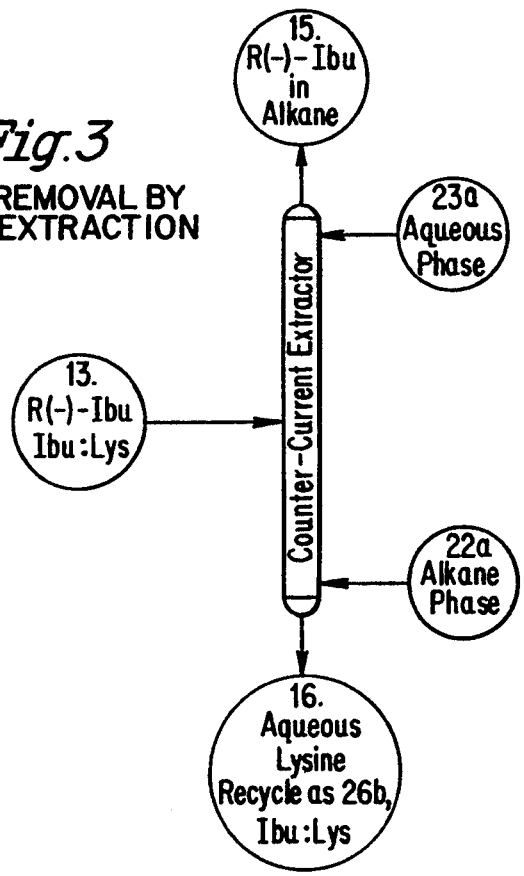
Figure 4:
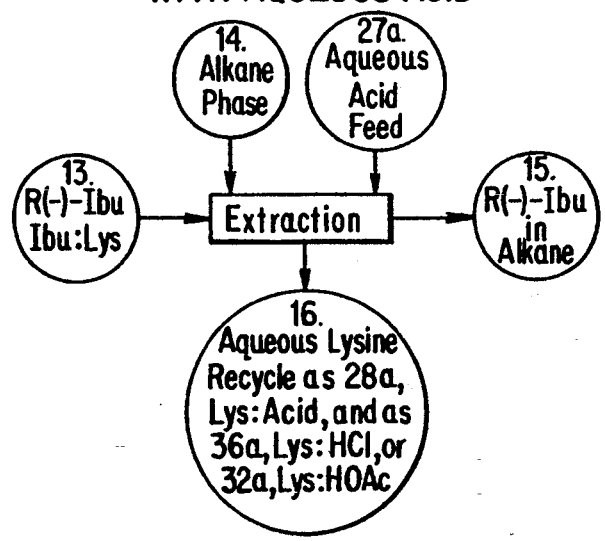

A molten mixture [stream 13, FIG. 2] containing S(+)-ibuprofen (0.2145 moles, 44.25 g), R(−)-ibuprofen (0.5763 moles, 118.89 g), and L-lysine (0.08603 moles, 12.577 g) is added to heptane [350 g, stream 14a] heated to 50° C. The resulting mixture is stirred for 15 minutes and then filtered at 50° C. to remove precipitated ibuprofen lysinate from the mother liquor. The filtered solid is washed with heptane [50 g, stream 14b]. The mother and wash liquors are combined to provide a mixture [stream 15] containing S(+)-ibuprofen (0.1912 moles, 39.43 g) and R(−)-ibuprofen (0.5136 moles, 105.95 g). The washed filtered solid is a second crop of ibuprofen lysinate and is dissolved in a mixture

[stream 23a] containing water (15 g), ethanol (76 g), and heptane (9 g). The resulting aqueous mixture [stream 16] contains ibuprofen lysinate (0.08603 moles, 30.32 g, ibuprofen S/R ratio of 27:73) and is recycled as stream 26a to the next batch's first crop crystallization of crude S(+)-ibuprofen lysinate.

EXAMPLE 6

Racemization and Distillation of R(−)-Enriched Ibuprofen

Heptane is removed as stream 18, FIG. 1, by distillation in an evaporator at atmospheric pressure from a mixture [stream 15, FIG. 1] containing S(+)-ibuprofen (0.1912 moles, 39.43 g), R(−)-ibuprofen (0.5136 moles, 105.95 g), and heptane (ca. 390 g). During the distillation, water [30 g, stream 17] is injected into the base of the evaporator to help strip out the last traces of heptane and to minimize formation of ibuprofen ethyl ester. The molten evaporation residue [stream 33], which consists essentially of ibuprofen with an S/R ratio of 27/73, is first racemized by being heated under nitrogen at 220° C. for four (4) hours and is then distilled at about 220° C., 10 mm HgA in an evaporator to provide a distillate [stream 19] of substantially pure racemized ibuprofen (0.6907 moles, 142.48 g, S/R ratio of 47:53) and an undistilled residue [stream 20, 2.91 g] for incineration as a waste stream. Racemized ibuprofen distillate [stream 19] is recycled to the first crop crystallization of crude S(+)-ibuprofen lysinate.

Heptane/water distillate stream 18 is allowed to phase in a decanter to provide a heptane upper phase [stream 14] and a water lower phase [stream 17].

EXAMPLE 7

Separation of Azeotrope Streams

Azeotrope distillate streams 21a-d are combined and allowed to separate into two liquid phases inside a decanter (FIG. 1). The alkane upper phase [stream 22] is a 94.8: 5.0: 0.2 mixture by weight of heptane, ethanol, and water. The aqueous lower phase [stream 23] is a 75.9: 15.0: 9.1 mixture by weight of ethanol, water, and heptane, a portion of which provides stream 23a. The remainder of the aqueous lower phase [stream 23] is distilled to provide a 92:8 by weight overhead mixture [stream 24] of ethanol and water and a heavy end [stream 25] of substantially pure water. A portion of heavy end water stream 25 is waste water stream 25c, which could be used as a pure water feed for other processes.

EXAMPLE 8

Extraction of Ibuprofen Lysinate from the Crystallization Liquor's Evaporation Residue with Water This procedure is an alternative to the above-described second crop crystallization of crude ibuprofen lysinate (Example 5). A molten mixture [stream 13, FIGS. 1, 3]containing S(+)-ibuprofen (0.2145 moles, 44.25 g), R(−)-ibuprofen (0.5763 moles, 118.89 g) and L-lysine (0.08603 moles, 12.577 g) is injected into the middle of a York-Scheibel-type counter-current extractor fed at the top with a mixture [stream 23a] containing water (15 g), ethanol (76 g), and heptane (9 g) and at the bottom with a mixture [stream 22c] containing heptane (350 g), ethanol (18.5 g), and water (0.73 g). The aqueous lower phase removed from the bottom of the extractor is a mixture [stream 16] containing ibuprofen lysinate (0.08603 moles, 30.32 g, ibuprofen S/R ratio of 27:73) and is recycled as stream 26b to the next batch's first crop crystallization of crude S(+)-ibuprofen lysinate. The alkane upper phase removed from the top of the extractor is a mixture [stream 15] containing S(+)-ibuprofen (0.1912 moles, 39.43 g) and R(−)-ibuprofen (0.5136 moles. 105.95 g) and is evaporated and racemized as described in Example 6, except that the evaporated solvent is recycled as azeotrope stream 21d and not as stream 18.

EXAMPLE 9

Extraction of Ibuprofen Lysinate from the Crystallization Liquor's Evaporation Residue with Aqueous HCl This procedure is an alternative to the above-described second crop crystallization of crude ibuprofen lysinate (Example 5). A molten mixture [stream 13, FIGS. 1, 4] containing S(+)-ibuprofen (0.2145 moles, 44.25 g), R(−)-ibuprofen (0.5763 moles, 118.89 g) and L-lysine (0.08603 moles, 12.577 g) is added to a 50° C. mixture containing heptane (400 g), water (16 g), and HCl (0.08603 mole, 3.137 g) [from streams 14 and 27a]. The resulting mixture is mixed thoroughly and then allowed to phase. The upper phase is a mixture [stream 15] containing ibuprofen (0.7908 moles, 163.13 g; S/R ratio of 27:73) and heptane (ca. 400 g). The lower phase is an aqueous mixture [stream 28a] containing lysine hydrochloride (0.08603 moles, 15.71 g) and is recycled as stream 36a to precipitation of NaCl from aqueous lysine (Example 1), or to ion exchange (Example 22) or electrodialysis (Example 23).

EXAMPLE 10

Extraction of Ibuprofen Lysinate from the Crystallization Liquor's Evaporation Residue with Aqueous Acetic Acid This procedure is an alternative to the above-described second crop crystallization of crude ibuprofen lysinate (Example 5). A molten mixture [stream 13, FIG. 4] containing S(+)-ibuprofen (0.2145 moles, 44.25 g), R(−)-ibuprofen (0.5763 moles, 118.89 g) and L-lysine (0.08603 moles, 12.577 g) is added to a 50° C. mixture containing heptane (400 g), water (167 g), and acetic acid (0.08603 mole, 5.166 g) [from streams 14 and 27a]. The resulting mixture is mixed thoroughly and then allowed to phase. The upper phase is a mixture [stream 15] containing ibuprofen (0.7908 moles, 163.13 g; S/R ratio of 27:73) and heptane (ca. 400 g). The lower phase is an aqueous mixture [stream 28a] containing lysine acetate (0.08603 moles, 17.743 g) and is recycled as stream 32a to lysine acetate cracking (Example 13 or 14).

EXAMPLE 11

Figure 5:
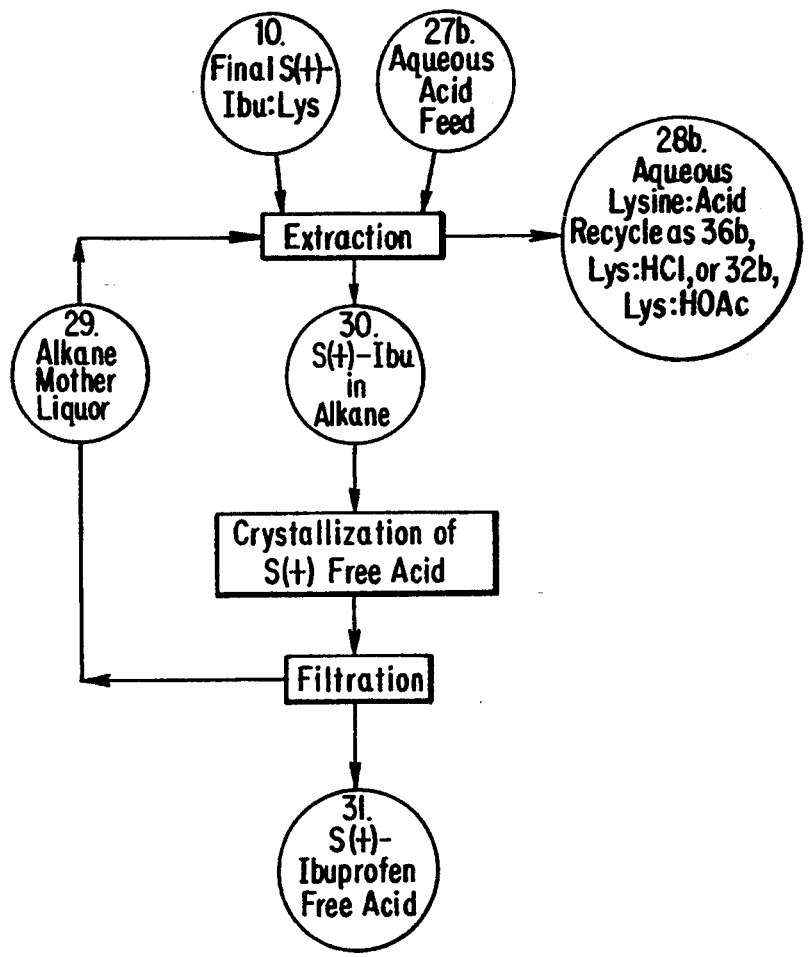

Conversion of S(+)-Ibuprofen Lysinate to S(+)-Ibuprofen Free Acid by Treatment with HCl A mixture of S(+)-ibuprofen lysinate (0.2837 mole, 100 g dry basis), heptane (88 g), S(+)-ibuprofen (8.53 mmole, 1.76 g), water (52 g), and HCl (0.2837 mole, 10.344 g) [from streams 10, 27b, and 29, FIG. 5] is mixed thoroughly at 60° C. and then allowed to phase. The lower phase is an aqueous mixture [stream 28b] containing lysine hydrochloride (0.2837 moles, 51.82 g) and is recycled as stream 36b to precipitation of NaCl from aqueous lysine (Example 1), to ion exchange (Example 22), or to electrodialysis (Example 23). The upper phase [stream 30] is a mixture containing S(+)-ibuprofen free acid (0.29223 moles, 60.283 g) and heptane (ca. 88 g) and is cooled from 60° C. to 0° C. to crystallize S(+)-ibuprofen free acid. The S(+)-ibuprofen free acid [stream 31, 0.2837 mole, 58.52 g] is removed by filtration from the heptane mother liquor [stream 29], which contains S(+)-ibuprofen (8.53 mmole, 1.76 g).

EXAMPLE 12

Conversion of S(+)-Ibuprofen Lysinate to S(+)-Ibuprofen Free Acid by Treatment with Acetic Acid A mixture of S(+)-ibuprofen lysinate (0.2837 mole, 100 g dry basis), heptane (88 g), S(+)-ibuprofen (8.53 mmole, 1.76 g), water (551 g), and acetic acid (0.2837 mole, 17.037 g) from streams 10, 27b, and 29, FIGS. 1, 5] is mixed thoroughly at 60° C. and then allowed to phase. The lower phase is an aqueous mixture [stream 28b] containing lysine acetate (0.2837 moles, 58.51 g) and is recycled as stream 32b to lysine acetate cracking (Example 13 or 14). The upper phase [stream 30] is a mixture containing S(+)-ibuprofen free acid (0.29223 moles, 60.283 g) and heptane (ca. 88 g) and is cooled from 60° C. to 0° C. to crystallize S(+)-ibuprofen free acid. The S(+)-ibuprofen free acid [stream 31, 0.2837 mole, 58.52 g] is removed by filtration from the heptane mother liquor [stream 29], which contains S(+)-ibuprofen (8.53 mmole, 1.76 g).

EXAMPLE 13

Lysine Acetate Cracking

To a stirred mixture [streams 32a,b, FIG. 6] containing lysine acetate (0.36973 moles, 76.254 g) and water (718 g) is added water [stream 25b, 54 g] and heptane [from stream 34] as an azeotrope [stream 35] of water, acetic acid, and heptane is removed by distillation at atmospheric pressure. The distillation residue [stream 5b] contains free lysine (0.36973 moles, 54.05 g) and water (54 g) for recycle to first crop crystallization (Example 2). Distillate stream 35 is allowed to phase in a decanter to provide a heptane upper phase [stream 34] and an aqueous acid lower phase [stream 27] containing acetic acid (0.36973 moles, 22.202 g) and water (718 g).

EXAMPLE 14

Lysine Acetate Cracking with Ibuprofen

To a stirred mixture containing racemic ibuprofen (0.36973 moles, 76.27 g), lysine acetate (0.36973 moles, 76.254 g) and water (718 g) [from streams 6b and 32a, b, FIG. 7] is added water [stream 25b, 150 g] and heptane [from stream 34] as an azeotrope [stream 35] of water, acetic acid, and heptane is removed by distillation at atmospheric pressure. The distillation residue [stream 26c] contains ibuprofen lysinate (0.36973 moles, 130.32 g) and water (150 g) for recycle to first crop crystallization (Example 2). Distillate stream 35 is allowed to phase in a decanter to provide a heptane upper phase [stream 34] and an aqueous acid lower phase [stream 27] containing acetic acid (0.36973 moles, 22.202 g) and water (718 g).

The following examples (15-21) and the subsequent discussion describe the other facet of this invention wherein there is provided a simple, unprecedented and highly efficient diastereoselective crystallization of either enantiomer of ibuprofen as its L-lysinate salt from a mixture of racemic ibuprofen and the same commercially available inexpensive resolving agent, L-lysine. The process obviates the shortcomings associated with both classical resolution (involving expensive synthetic resolving agents) and enzyme technology. The process also produces the enantiomerically enriched ibuprofen directly as the preferred lysinate salt which is desirable for human consumption, thereby avoiding the obligatory separation of ibuprofen (free enantiomer) from a chiral auxiliary. As chemical resolution technology continues to play a dominant role (despite increasing competition from the enzymatic methods), the potential offered by such selective crystallization technology is substantial.

EXAMPLE 15

Preparation of Free Aqueous L-Lysine from L-Lysine Hydrochloride

A chromatography column was packed with 68.6 gM of Amberlyre IRA-400 (OH) ion exchange resin (capacity 1.6 m eq./gM). The resin was washed with 25 mL water. A solution of L-lysine monohydrochloride (18.2 gM) dissolved in 35 mL of water was added to the top of the column. The column was eluted with 200 mL water and the combined aqueous fractions were concentrated in the rotovapor to total dryness, producing 13.31 g (92% yield) of L-lysine which was used in the selective crystallization process without further purification.

EXAMPLE 16

Selective Crystallization of S-Ibuprofen L-Lysinate Utilizing L-Lysine

Racemic (RS)-ibuprofen (41.25 g, 0.20 tool) was dissolved in ethanol (140 mL). The solution was cooled to 0° C. L-lysine (11.7 g, 0,080 Mol dissolved in 7 mL water) was added to this solution via addition funnel while the solution temperature was maintained at 0° C. The solution was seeded with S-ibuprofen L-lysinate (0.1 g). The resulting mixture was stirred at 0° C. for four (4) hours. The crystals were filtered, washed with ice-cold (2° C.) ethanol (40 mL) and dried under vacuum overnight to produce 19.64 g (70% yield based on L-lysine) of S-ibuprofen L-lysinate salt in 94% diastereomeric purity as evidenced by chiral HPLC.

EXAMPLE 17

Recrystallization to Produce Diastereomerically Pure S-Ibuprofen L-Lysinate 2 g of S-ibuprofen L-lysinate (94% diastereomeric purity; obtained from Example 16) was dissolved in a mixture of ethanol (12 mL) and water (1.2 mL) at 60° C. The mixture was slowly cooled from 60° C. to 0° C. over a period of two (2) hours and stirred at 0° C. for two (2) hours. The crystals were filtered, washed with cold (0° C.) ethanol (6 ml) and dried under vacuum overnight to produce 1.8 g (95% yield of the available S-salt) of the S-ibuprofen L-lysinate in >99% diastereomeric purity. (The slow gradual temperature gradient during the cooling process is essential to obtain the required diastereomeric purity. Thus, when the crystallization mixture was cooled at a faster rate (ca. 20 minutes) the diastereomeric purity of the product was only 97%).

EXAMPLE 18

Selective Crystallization of R-Ibuprofen L-Lysinate

Racemic (RS)-ibuprofen (41.25 g, 0.20 Mol) was dissolved in ethanol (140 mL). The solution was cooled to 12° C. L-lysine (11.7 g, 0.080 Mol dissolved in 7 mL water) was added to this solution via addition funnel while the solution temperature was maintained at 12° C. The resulting mixture was stirred at 22° C. for 48 hours. The crystals were filtered, washed with ethanol (40 mL) and dried under vacuum overnight to produce 19.6 g (70% yield based on L-lysine) of R-ibuprofen L-lysinate salt in 98% diastereomeric purity as evidenced by chiral HPLC. The salt was recrystallized from ethanol/water as described in Example 17 to produce 17.3 g (89% yield of the available R-salt) of the R-ibuprofen L-lysinate in >99% diastereomeric purity.

EXAMPLE 19

Preparation of S-Ibuprofen from S-Ibuprofen Lysinate 35.2 g of S-ibuprofen/lysinate (99% d.e.) was dissolved in 300 mL water at 22° C. The pH of the resulting solution was adjusted to one (1) via addition of concentrated aq. Hcl. The mixture was stirred for one (1) hour at 22° C. The heterogeneous mixture was filtered. The crystals were dried at 50° C. under vacuum to produce 20.6 g of S(+) ibuprofen (100% yield) of 99% enantiomeric excess as evidenced by chiral HPLC. The mother liquor containing L-lysine hydrochloride was recycled to the ion exchange lysine recovery process described in Example 15.

EXAMPLE 20

Preparation of R-Ibuprofen from R-Ibuprofen Lysinate 35.2 g of R-ibuprofen/lysinate (99% d.e.) was subjected to the same process as described in Example 19 to produce 20.6 g of R-ibuprofen (100% yield) in 99% enantiomeric purity as evidenced by chiral HPLC.

EXAMPLE 21

Selective Crystallization of R-Ibuprofen L-Lysinate

Racemic (RS)-ibuprofen (41.25 g, 0.20 Mol) was dissolved in ethanol (140 mL). The solution was held at 22° C. while L-lysine (11.7 g, 0.080 Mol dissolved in 7 mL water) was added by addition funnel. The resulting mixture was seeded with R-ibuprofen L-lysinate crystals and then stirred at 22° C. for 48 hours. The precipitated crystals were filtered, washed with ethanol (40 mL,) and dried under vacuum overnight to produce 19.1 g (68% yield based on L-lysine) of R-ibuprofen L-lysinate salt in 98% diastereomeric purity as evidenced by chiral HPLC. The salt was recrystallized from ethanol/water as described in Example 17 to produce 17.4 g (92% yield of the available R-salt) of the R-ibuprofen L-lysinate in >99% diastereomeric purity.

DISCUSSION OF EXAMPLES 16–21

As previously mentioned, RS-ibuprofen belongs to a class of non-steroidal anti-inflammatory agents that has remained an area of intense study. S(+)-ibuprofen is the pharmacologically active component of RS-ibuprofen. The R(−) isomer is either inactive or weakly active in vitro although the difference in activity is markedly decreased in vitro due to metabolic inversion of the R(−) to the active S(+) enantiomer. On the other hand, R(−)-ibuprofen, the therapeutically inactive isomer, is expected to give less gastrointestinal side effects than the racemate, while still retaining its anti-inflammatory activity via metabolic inversion to the active S(+)-isomer. In order to realize enhanced specificity, avert undesirable load on metabolism, and minimize gastrointestinal side effects, it is desirable to market S(+) ibuprofen in the form of its lysinate salt.

In light of such continuing interest in the area of S(+) ibuprofen, coupled with the recent demand for enantiomerically pure drugs in chemotherapy, an efficient preferential resolution of racemic (RS) ibuprofen is highly desirable. The existing methods for resolving RS-ibuprofen via fractional crystallization of diastereomeric salts with chiral amine (e.g. α-methylbenzylamine, L-lysine) suffer from the following disadvantages: (1) the maximum theoretical yield is only 50% (based on the chiral auxiliary), thus requiring additional steps for efficiently recovering and recycling the resolving agent, as well as the unwanted enantiomer; (2) although synthetic resolving agents (e.g. α-methylbenzylamine) are available in both enantiomeric forms, naturally occurring agents (e.g. L-lysine) are often only available in one (1) enantiomeric form, thereby limiting the scope of such diastereomeric separations.

This facet of the present invention describes an unprecedented selective crystallization of ibuprofen lysinate from one (1) mole of racemic ibuprofen and ≦0.5 mole of L-lysine which enables the preparation of either enantiomer of ibuprofen (as well as the preferred lysinate salt) utilizing the inexpensive, naturally occurring and readily available S-lysine as the chiral resolving agent and appropriate choice of resolution conditions. The cost of naturally occurring L-lysine (available as the hydrochloride salt from Archer Daniel Midland Company in 98.5% chemical purity and 100% optical purity) is $2.00/Kg., whereas the enantiomeric D-lysine, which is required for the production of R-(−)-ibuprofen via traditional classical resolution, costs $8000.00/Kg.

It has been unexpectedly found that in the selective crystallization of S-ibuprofen/L-lysinate salt with not more than one (1) mole of L-lysine per mole of S-ibuprofen in the crystallization medium, the S-ibuprofen L-lysinate salt diastereomer crystallizes much more rapidly than does the R-ibuprofen L-lysinate salt diastereomer, thereby leaving the mother liquor enriched in R-ibuprofen as shown in Scheme 1 below.

Scheme 1

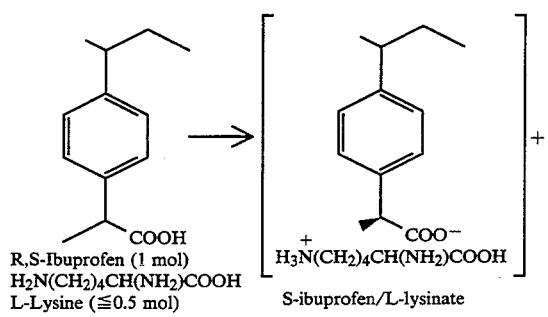

R,S-Ibuprofen (1 mol)
H$_2$N(CH$_2$)$_4$CH(NH$_2$)COOH
L-Lysine (≦0.5 mol)

S-ibuprofen/L-lysinate

Scheme 1 (continued)

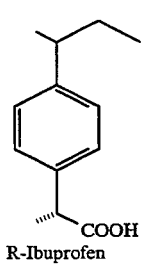

R-Ibuprofen

Crystallization studies were conducted (as shown in Examples 15-20) by adding an aqueous solution of L-lysine to an ethanolic solution of RS-ibuprofen followed by seeding. The diastereomeric excesses (d.e.) of the crystals (sampled at one (1) hour time intervals) were monitored by chiral HPLC analysis. Optimization with respect to temperature (0° C.), time (4 to 6 hours), lysine:S(+)-ibuprofen mole ratio (0.8:1), ethanol volume (3.8 ml. per gram combined weight of both ibuprofen enantiomers) and water concentration (5 wt. % with respect to ethanol) afforded a 70% isolated yield (based on available lysine) of S-ibuprofen lysinate in 94:6 diastereomer ratio (88% diastereomeric excess (d.e.)). The product of the first crystallization can be recrystallized once from aqueous ethanol (90 wt %) to afford ibuprofen lysinate monohydrate in 99% d.e. Maintaining the water content at about 10 wt % in the aqueous ethanol during the recrystallization is imperative to obtain the required monohydrate form in a reproducible manner.

Particularly noteworthy and remarkable in this invention is the fact that a complete reversal of diastereoselectivity was observed when the crystallization was conducted at 22° C. for 48 hours under otherwise identical conditions, thereby producing the R-ibuprofen/L-lysinate in 99:1 diastereomer ratio (98% d.e.). The same diastereoreversal was also observed when the heterogeneous crystallization mixture obtained after four (4) hours at 0° C. (where the isolated crystals were diastereomerically enriched in S-ibuprofen/L-lysinate) was allowed to stir at ambient temperature (22° C.) for an additional 48 hours as depicted in Scheme 2. Selective precipitation of the R-ibuprofen/L-lysinate would allow direct recovery of S(+)-ibuprofen as the free acid from the mother liquor.

Scheme 2

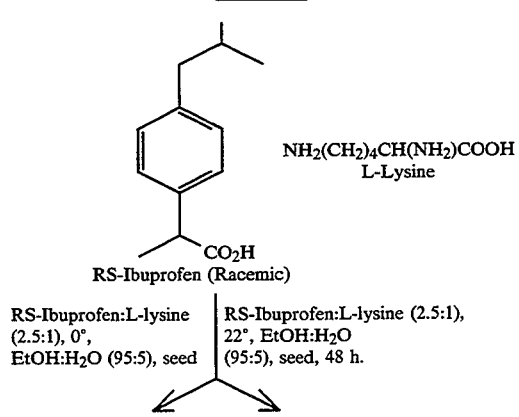

Scheme 2 (continued)

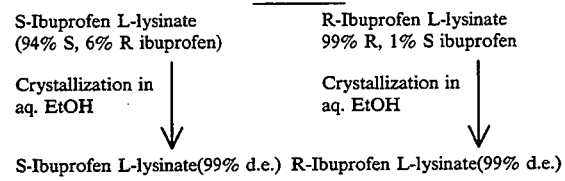

S-Ibuprofen L-lysinate(99% d.e.)   R-Ibuprofen L-lysinate(99% d.e.)

Figure 8:
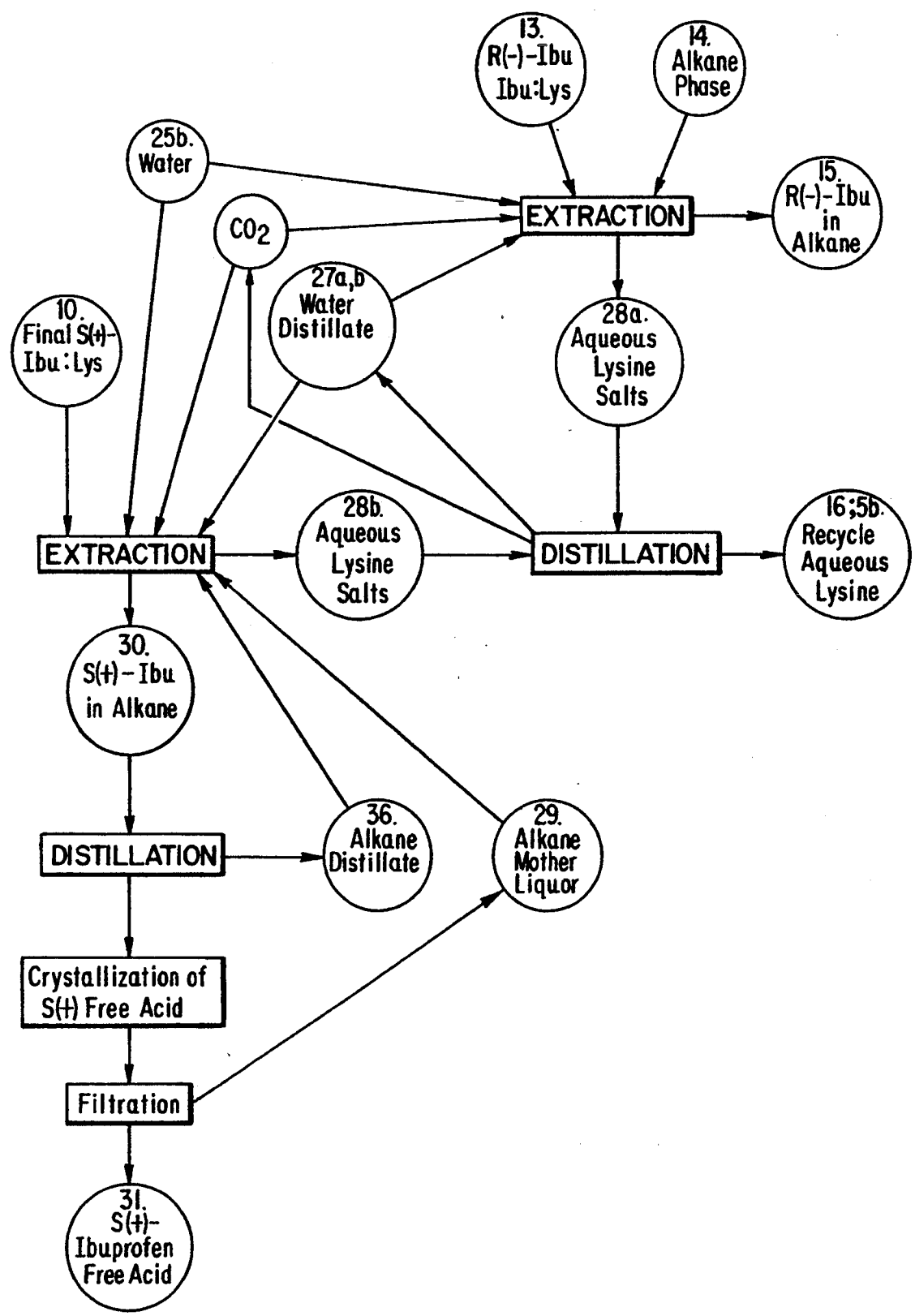

The following examples 22-27 illustrate another facet of the present invention and disclose recovery of the free aqueous lysine with carbon dioxide and the purification of various by-product/recycle streams and the separation of various materials from each other. Reference is also made to FIG. 8 for Examples 24-27.

EXAMPLE 22

Free Aqueous Lysine from Ion Exchange

A solution of L-lysine hydrochloride (0.36973 mole, 67.532 g) in water (68 g) [from stream 36a in Example 9 and stream 36b in Example 11] is added to the top of a column of Amberlyte IRA-400(OH) ion exchange resin (254.54 g, 0.4073 equivalents) prewashed with water. The column is subsequently eluted with water (742 g) to provide an aqueous solution of free L-lysine from which water is partially evaporated at 60° C. and 20 mm HgA pressure. The resulting evaporation residue [stream 5a] contains free L-lysine (0.36973 moles, 54.05 g) and water (54 g) for recycle to first crop crystallization (Example 2).

The ion exchange column is regenerated by reverse elution with a solution of sodium hydroxide (0.4067 mole, 16.27 g) in water (68 g) to produce a solution of sodium chloride (0.36973 mole, 21.608 g) in water (68 g) [stream 4]. The ion exchange column is then eluted with water to remove residual sodium hydroxide prior to addition of the next batch of lysine hydrochloride.

EXAMPLE 23

Generation of Free Aqueous Lysine by Electrodialysis with Permselective Membranes A solution of L-lysine hydrochloride (0.36973 mole, 67.532 g) in water (68 g) [from stream 36a in Example 9 and stream 36b in Example 11] is subjected to electrodialysis with permselective membranes according to the procedure described in Example 9 of U.S. Pat. No. 3,330,749, the entire contents of which are incorporated herein by reference. The resulting aqueous solution of free L-lysine in compartment A is partially evaporated at 60° C. and 20 mm HgA pressure to provide an evaporation residue [stream 5a] containing free L-lysine (0.36973 moles, 54.05 g) and water (54 g) for recycle to first crop crystallization (Example 2). The aqueous solution of hydrochloric acid (0.36973 moles) in compartment C is stream 4.

EXAMPLE 24

Extraction of Ibuprofen Lysinate from the Crystallization Liquor's Evaporation Residue with Aqueous Carbonic Acid This procedure is an alternative to the procedures described in Examples 5, 8, 9, and 10 above. A molten mixture [stream 13, FIGS. 1 and 8] containing S(+)-ibuprofen (0.2145 moles, 44.25 g), R(−)-ibuprofen (0.5763 moles, 118.89 g), and L-lysine (0.08603 moles, 12.577 g) is added to a mixture containing heptane (400 g) and water (30.32 g) [from streams 14, 25b, and 27a]. The resulting mixture is mixed thoroughly at 40° C. under 1000 psi partial pressure of carbon dioxide and then allowed to phase. The lower phase is separated from the upper phase under 1000 psi carbon dioxide pressure. The upper phase is a mixture [stream 15] containing ibuprofen (0.7908 moles, 163.13 g; S/R ratio of 27.73) and heptane (ca. 400 g). The lower phase is an aqueous mixture [stream 28a] containing lysine (0.08603 moles, presumably as bicarbonate, carbonate, and/or carbamate salts) and water (30.32 g) and is then recycled to carbonate/carbamate cracking of Examples 26 or 27.

EXAMPLE 25

Conversion of S(+)-Ibuprofen Lysinate to S(+)-Ibuprofen Free Acid by Treatment with Aqueous Carbonic Acid This procedure is an alternative to the procedures described in Examples 11 and 12 above. A mixture of S(+)-ibuprofen lysinate (0.2837 mole, 100 g dry basis), heptane (155 g), S(+)-ibuprofen (8.53 mmole, 1.760 g), and water (100 g) [from streams 10, 25b, 27b, 29, and 36; FIGS. 1 and 8] is mixed thoroughly at 40° C. under 1000 psi partial pressure of carbon dioxide and then allowed to phase. The lower phase is separated from the upper phase under 1000 psi carbon dioxide pressure. The lower phase is an aqueous mixture [stream 28b] containing lysine (0.2837 moles, presumably as bicarbonate, carbonate, and/or carbamate salts) and water (100 g) and is recycled to carbonate/carbamate cracking Example 26 or 27.

The upper phase [stream 30] is a mixture containing S(+)-ibuprofen free acid (0.29223 moles, 60,283 g) and heptane (ca. 155 g). Heptane [stream 36, 68 g] is removed from the upper phase by distillation at atmospheric pressure. The concentrated upper phase is then cooled to 0° C. to crystallize S(+)-ibuprofen free acid. The crystalline S(+)-ibuprofen free acid [stream 31, 0.2837 mole, 58.524 g] is removed by filtration from the heptane mother liquor [stream 29], which contains S(+)-ibuprofen (8.53 mmole, 1.760 g) and heptane (87 g).

EXAMPLE 26

Lysine Carbamate/Carbonate Cracking

This procedure is used in combination with Examples 24 and/or 25 above and is an alternative to the procedures described in Examples 13 and 14 above. From a stirred mixture [streams 28a and 28b, FIG. 8] containing lysine (0.36973 moles, presumably as bicarbonate, carbonate, and/or carbamate salts) and water (130.32 g) is removed a water distillate [streams 27a and 27b, 76.32 g total] by distillation at atmospheric pressure. During this distillation, the salts of lysine are converted to free aqueous lysine and carbon dioxide, and carbon dioxide is removed with water by the distillation. The distillation residue [stream 16] contains free lysine (0.36973 moles, 54.05 g) and water (54 g) for recycle [as stream 5b] to first crop crystallization (Example 2).

EXAMPLE 27

Lysine Carbamate/Carbonate Cracking with Ibuprofen

This procedure is used in combination with Examples 24 and/or 25 above and is an alternative to the procedures described in Examples 13, 14, and 26 above. Substantially racemic ibuprofen (0.36973 moles) is added to a stirred mixture [streams 28a and 28b, FIG. 8] containing lysine (0.36973 moles, presumably as bicarbonate, carbonate, and/or carbamate salts) and water (130.32 g) at about 40° C. As the ibuprofen dissolves, bicarbonate, carbonate, and/or carbamate salts of lysine are converted to aqueous ibuprofen lysinate and carbon dioxide, the later of which is swept out of the reaction mixture with nitrogen gas. After substantially complete removal of carbon dioxide, the reaction mixture [stream 16] contains ibuprofen lysinate salt (0.36973 moles, 130.322 g) and water (130.32 g) for recycle [as stream 26c] to first crop crystallization (Example 2).

Although the free L-lysine feed [stream 5a] to the first crop crystallization (Example 2) may be purchased commercially (Aldrich Chemical Co.), L-lysine salts (such as the hydrogen sulfate and particularly the hydrogen chloride salts) are much cheaper than free lysine and can be converted to free aqueous lysine by procedures described in Examples 1, 22, and 23. Furthermore, the present invention does not require total removal of the negative counterion (e.g., chloride, in Examples 1, 22, and 23) of the protonated L-lysine cation feed (e.g., L-lysine hydrochloride in Examples 1, 22, and 23) from which the free aqueous L-lysine is generated. When the free aqueous L-lysine (e.g., stream 5a from Examples 1, 22, or 23) contains a portion of this negative counterion as an impurity, much of that impurity remains with the first crop crystallization's mother and wash liquors (streams 7 and 8, respectively, from Example 2), thereby avoiding or alleviating contamination of the crude S(+)-ibuprofen lysinate (stream 9 from Example 2). This negative counterion impurity can be purged from the process in stream 4 by processing and recycle of streams 7 and 8 to Examples 1, 22, or 23 as described in Examples 4, 9, and 11. Other impurities in the free aqueous L-lysine feed [stream 5a] to first crop crystallization might also be separated from desired product and purged from the process in a similar fashion.

Thus, in one embodiment of the present invention, there is provided a process to selectively crystallize a salt of an optically active amino acid and optically active ibuprofen, said process comprising, (1) providing a reaction mixture containing first and second enantiomers of ibuprofen, a solvent mixture, and a molar quantity of said amino acid such that the molar quantity of said amino acid is no greater than about the molar quantity of one of said enantiomers of said ibuprofen; (2) precipitating from said mixture at a temperature below about 5° C.; a salt enriched in one enantiomer of ibuprofen; said amino acid is selected from the group consisting of lysine, arginine, and histidine.

In another embodiment of the present invention, there is an additional step to the process as follows: (3) holding the reaction mixture containing said precipitated salt for a sufficient period of time and at a temperature above about 5° C. whereby said precipitated salt redissolves into said reaction mixture and the other enantiomer of said ibuprofen precipitates out as a salt. In either of the above embodiments, the amino acid can be lysine.

Advantages of the present process for production of S(+)-ibuprofen lysinate salt from free L-lysine include the following. Use of L-lysine in a molar quantity no greater than the molar quantity of the S(+) enantiomer of the ibuprofen feed obviates any and all consumption of other chemicals as well as any and all processing steps involving other chemicals (except solvents). Another advantage of the present process is that its only two waste streams are (1) substantially pure water [stream 25c] in a quantity equal to the water content of fresh lysine feed and (2) a small amount (about 2% by weight of the final ibuprofen lysinate product), of completely combustible organic residue [stream 20] from distillation of racemized ibuprofen. These advantages are consequences of the fact that most of the R(−)ibuprofen [stream 15] is never converted to an amine salt before racemization and recycle, thereby permitting (Example 5 or 8) the rest of the R(−)-ibuprofen [in stream 26a or 26b, respectively] to be recycled as lysinate salt without racemization. Another advantage is that the ibuprofen S/R enantiomer ratio is high (92:8 to 98:2) in the first crop of crude S(+)-ibuprofen lysinate salt and is readily increased to >200 by a single recrystallization of the crude salt. Another advantage is that efficient racemization of R-enriched ibuprofen is achieved thermally without use of any chemicals, solvents, or chemical treatment. No prior art process has all of these advantages.

In another preferred embodiment of the present invention, there is provided a process for preparing a first salt of an amino acid and an α-arylcarboxylic acid of the formula Ar(R)CHCO$_2$H, from a second salt of an anion and a protonated cation of said amino acid, said process comprising: combining water, a base, and said protonated cation of said amino acid to produce an aqueous solution of said amino acid; separating said aqueous solution of said amino acid from a first portion of said anion; precipitating said first salt of said amino acid and said α-arylcarboxylic acid from a mixture incorporating said aqueous solution of said amino acid, and separating said first salt from a second portion of said anion; wherein R is selected from the group consisting of $C_1$–$C_8$ alkyl and $C_1$–$C_8$ substituted alkyl; Ar is selected from the group consisting of phenyl, substituted phenyl, 2-naphthyl, substituted 2-naphthyl, 2-fluorenyl, and substituted 2-fluorenyl; and said amino acid is selected from the group consisting of lysine, arginine, and histidine.

In the above process, the anion can be chloride and the base can be a hydroxide ion or an ion exchange resin. Also, the aqueous solution of said amino acid can be separated from said first portion of said anion with a pennselective membrane.

In still another preferred embodiment of the present invention, there is provided a process for preparing a first salt of an amino acid and an α-arylcarboxylic acid of the formula Ar(R)CHCO$_2$H, from a second salt of an anion and a protonated cation of said amino acid, said process comprising: combining water, a base, and said protonated cation of said amino acid to produce an aqueous solution of said amino acid; separating said aqueous solution of said amino acid from at least a portion of said anion; combining said α-arylcarboxylic acid with said aqueous solution of said amino acid to produce a mixture containing said first salt of said amino acid and said α-arylcarboxylic acid; and combining said base with at least one component of said mixture to at least partially regenerate said aqueous solution of said amino acid; wherein R is selected from the group consisting of $C_1$–$C_8$ alkyl and $C_1$–$C_8$ substituted alkyl; Ar is selected from the group consisting of phenyl, substituted phenyl, 2-naphthyl, substituted 2-naphthyl, 2-fluorenyl, and substituted 2-fluorenyl; and said amino acid is selected from the group consisting of lysine, arginine, and histidine.

In this process said component can contain said anion or said protonated cation of said amino acid. The base can be a hydrogen ion or an ion exchange resin. In this process, the aqueous solution of said amino acid can be separated from said portion of said anion with an ion exchange resin or with a permselective membrane. Furthermore, a portion of said anion can be separated as a solid salt from said aqueous solution of said amino acid. In this process, there can be further steps of isolating said first salt from said mixture, combining said first salt with a third acid, other than said amino acid and said α-aryl carboxylic acid, to produce said α-arylcarboxylic acid in an enantiomerically enriched form and said protonated cation of said amino acid, and separating said enantiomerically enriched α-arylcarboxylic acid from said protonated cation of said amino acid, wherein said component is said protonated cation of said amino acid.

In another preferred embodiment of the present invention, there is provided a process for preparing a salt of an amino acid and an α-arylcarboxylic acid Ar(R)CHCO$_2$H, said process comprising: distilling water from a mixture containing said amino acid and said ct-arylcarboxylic acid and then precipitating said salt from said mixture, wherein R is selected from the group consisting of $C_1$–$C_8$ alkyl and $C_1$–$C_8$ substituted alkyl; Ar is selected from the group consisting of phenyl, substituted phenyl, 2-naphthyl, substituted 2-naphthyl, 2-fluorenyl, and substituted 2-fluorenyl; and said amino acid is selected from the group consisting of lysine, arginine, and histidine. In this process, a water-immiscible azeotroping agent can be added to said mixture to assist said distillation, and the distillation produces a distillate containing two (2) liquid phases which axe allowed to separate and axe then recycled independently.

What is claimed is:

1. In a process to selectively crystallize a salt of an optically active amino acid and an optically active α-arylcarboxylic acid of the formula Ar(R)CHCO$_2$H from a reaction mixture comprising said optically active amino acid and first and second enantiomers of said α-arylcarboxylic acid, the improvement comprising: (1) providing a reaction mixture containing first and second enantiomers of said α-arylcarboxylic acid and a molar quantity of said optically active amino acid, such that the molar quantity of said optically active amino acid is no greater than about the molar quantity of one of said enantiomers of said α-arylcarboxylic acid; and (2) precipitating from said reaction mixture a salt enriched in said first enantiomer of said α-arylcarboxylic acid; wherein R is selected from the group consisting of $C_1$ to $C_8$ alkyl and $C_1$ to $C_8$ substituted alkyl; Ar is selected from the group consisting of phenyl, substituted phenyl, 2-naphthyl, substituted 2-naphthyl, 2-fluorenyl, and substituted 2-fluorenyl; and said amino acid is selected from the group consisting of lysine, arginine, and histidine.

2. The improvement of claim 1 wherein there is an additional step as follows: (3) holding the reaction mixture, containing said precipitated salt, for a sufficient period of time and temperature whereby said precipitated salt redissolves into said reaction mixture and a salt enriched in said second enantiomer of said α-arylcarboxylic acid precipitates.

3. The improvement of claim 2 wherein said salt precipitated in step 3 is separated from the reaction mixture.

4. The improvement of claim 2 wherein the temperature, in step 3, is greater than about 5° C.

5. The improvement of claim 2 wherein the temperature, in step 3, is from about 15° C. to about 25° C., and the temperature of the reaction mixture, in step 2, is less than about 10° C.

6. The improvement of claim 1 wherein the α-arylcarboxylic acid is ibuprofen.

7. The improvement of claim 1 wherein the α-arylcarboxylic acid is naproxen.

8. The improvement of claim 1 wherein the α-arylcarboxylic acid is fenoprofen.

9. The improvement of claim 1 wherein the α-arylcarboxylic acid is indoprofen.

10. The improvement of claim 1 wherein the α-arylcarboxylic acid is ketoprofen.

11. The improvement of claim 1 wherein the α-arylcarboxylic acid is selected from the group consisting of flurbiprofen, pirprofen, suprofen, cicloprofen, and minoxiprofen.

12. The improvement in claim 1 wherein the temperature of the reaction mixture is maintained at about 15° C. to about 25° C.

13. The improvement in claim 12 and further comprising the step of separating the precipitated salt from the reaction mixture after the precipitation takes place over a time of from about eight hours to about 96 hours.

14. The improvement in claim 1 wherein the temperature of the reaction mixture is maintained at about −10° C. to about +10° C.

15. The improvement in claim 14 and further comprising the step of separating the precipitated salt from the reaction mixture after the precipitation takes place over a time of from about 0.25 hours to about eight hours.

16. The improvement of claim 1, wherein the quantity of said first enantiomer in said mixture is no greater than about the quantity of said second enantiomer.

17. The improvement of claim 1, wherein said salt is further acidified to said α-aryl caxboxylic acid.

18. The improvement of claim 1 wherein said precipitated salt is contacted with an organic acid to produce said first enantiomer in free acid form and thereafter separating said free acid from the reaction mixture.

19. The improvement of claim I wherein said reaction mixture additionally contains a solvent mixture which comprises water and an alcohol which can dissolve said α-arylcarboxylic acid.

20. The improvement of claim 19 wherein, (a) the solvent mixture comprises water and ethanol, (b) the α-arylcarboxylic acid is ibuprofen, and (c) the amino acid is lysine.

21. The improvement of claim 1 wherein the reaction mixture is at a temperature of above about 5° C.

22. The improvement of claim 21 wherein, prior to the precipitation step, there are added crystals of the desired salt to act as a seed for precipitation of the desired salt.

23. The improvement of claim 21 wherein the α-arylcarboxylic acid is ibuprofen.

24. The improvement of claim 21 wherein the ≠-arylcarboxylic acid is selected from the group consisting of naproxen, fenoprofen, indoprofen, ketoprofen, flurbiprofen, purprofen, suprofen, cicloprofen, minoxiprofen, coprofen, benoxaprofen, bisiprofenum, fluprofen, clidmac, tertiprofen, hexaprofen, mexoprofen, and pranoproflem.

25. The improvement of claim 3 wherein the reaction mixture in step 3, after separation from the precipitated salt, is recycled to the step 1 process.

26. The improvement of claim 1 wherein the precipitated salt formed in step 2 is separated from the reaction mixture and then such reaction mixture is recycled to the step 1 process.

27. A process to selectively crystallize a salt of an optically active amino acid and optically active ibuprofen, said process comprising, (1) providing a reaction mixture containing first and second enantiomers of ibuprofen, a solvent mixture, and a molar quantity of said amino acid such that the molar quantity of said amino acid is no greater than about the molar quantity of one of said enantiomers of said ibuprofen; (2) precipitating from said mixture at a temperature below about 5° C., a salt enriched in one enantiomer of ibuprofen; said amino acid is selected from the group consisting of lysine, arginine, and histidine.

28. The process as set forth in claim 27 wherein there is an additional step as follows: (3) holding the reaction mixture containing said precipitated salt for a sufficient period of time and at a temperature above about 5° C. whereby said precipitated salt redissolves into said reaction mixture and the other enantiomer of said ibuprofen precipitates out as a salt.

29. The process as set forth in claim 27 wherein the amino acid is lysine.

* * * * *